US011986460B2

(12) United States Patent
Jain et al.

(10) Patent No.: US 11,986,460 B2
(45) Date of Patent: May 21, 2024

(54) SOLID PHARMACEUTICAL PREPARATION CONTAINING LIPOIC ACID AND USE THEREOF

(71) Applicant: The Procter & Gamble Company, Cincinnati, OH (US)

(72) Inventors: Satishkumar Jain, Thane (IN); Parminder Singh Sidhu, Darmstadt (DE); Paul Robinson, East Yorkshire (GB); Madhura Rege, Mumbai (IN); Sundareswarakumar Chellaswamy, Tamil Nadu (IN)

(73) Assignee: The Procter & Gamble Company, Cincinnati, OH (US)

( * ) Notice: Subject to any disclaimer, the term of this patent is extended or adjusted under 35 U.S.C. 154(b) by 79 days.

(21) Appl. No.: 16/695,710

(22) Filed: Nov. 26, 2019

(65) Prior Publication Data

US 2020/0163934 A1 May 28, 2020

(30) Foreign Application Priority Data

Nov. 26, 2018 (IN) .............................. 201831044436

(51) Int. Cl.
| A61K 31/385 | (2006.01) |
| A61K 47/02 | (2006.01) |
| A61K 47/22 | (2006.01) |
| A61K 47/24 | (2006.01) |
| A61K 47/32 | (2006.01) |
| A61K 47/34 | (2017.01) |

(52) U.S. Cl.
CPC ............ *A61K 31/385* (2013.01); *A61K 47/02* (2013.01); *A61K 47/22* (2013.01); *A61K 47/24* (2013.01); *A61K 47/32* (2013.01); *A61K 47/34* (2013.01)

(58) Field of Classification Search
CPC ...... A61K 31/385; A61K 47/02; A61K 47/22; A61K 47/24; A61K 47/32; A61K 47/34; A61K 31/51; A61K 31/4415; A61K 31/714; A61K 9/2009; A61K 9/2027; A61K 9/1611

See application file for complete search history.

(56) References Cited

U.S. PATENT DOCUMENTS

| 5,085,498 | A | 2/1992 | Yamamoto |
| 6,495,177 | B1 | 12/2002 | Devries |
| 8,728,535 | B2 | 5/2014 | Squashic |
| 9,248,096 | B2 | 2/2016 | Howard |
| 9,278,109 | B2 | 3/2016 | Gonzalez |
| 9,474,721 | B2 | 10/2016 | Hamed |
| 2002/0102301 | A1 | 8/2002 | Schwarz |
| 2005/0085498 | A1* | 4/2005 | Byrd ....................... A61P 25/16 514/275 |
| 2005/0147620 | A1 | 7/2005 | Bozicevic |
| 2009/0252787 | A1 | 10/2009 | Pasha |
| 2009/0270469 | A1 | 10/2009 | Gant |
| 2011/0117194 | A1 | 5/2011 | Kim |
| 2011/0160150 | A1* | 6/2011 | Haley .................. A61K 31/198 514/21.9 |
| 2012/0232167 | A1 | 9/2012 | Takeuchi et al. |
| 2013/0084272 | A1 | 4/2013 | Perrin |
| 2014/0271890 | A1 | 9/2014 | Ahmad |
| 2017/0304195 | A1 | 10/2017 | Föger |
| 2018/0344687 | A1 | 12/2018 | Emerson |

FOREIGN PATENT DOCUMENTS

| DE | 4317646 A1 | 12/1994 |
| DE | 19938098 A1 | 2/2001 |
| EP | 0858802 A2 | 8/1998 |
| EP | 1082107 B1 | 10/2005 |
| EP | 1585502 B1 | 6/2011 |
| EP | 2838529 B1 | 3/2016 |
| EP | 2651251 B1 | 6/2016 |
| EP | 2572705 B1 | 9/2017 |
| IN | 01334MU2010 A | 1/2010 |
| WO | WO9961004 A1 | 12/1999 |
| WO | WO03079819 A1 | 10/2003 |
| WO | WO03084532 A1 | 10/2003 |
| WO | WO2013115739 A1 | 8/2013 |
| WO | WO2014135956 A1 | 9/2014 |
| WO | WO2019058273 A1 | 3/2019 |
| WO | WO2019087054 A1 | 5/2019 |

OTHER PUBLICATIONS

PCT Search Report for PCT/US2019/063135 dated Feb. 6, 2020.
Bühler, "Vinylpyrrolidone-vinyl acetate copolymer (Copovidone)", Polyvinylpyrrolidone Excipients for Pharmaceuticals, https://doi.org/10.1007/3-540-27090-6_4, Dec. 8, 2004, pp. 179-219.

* cited by examiner

*Primary Examiner* — Kortney L. Klinkel
*Assistant Examiner* — Padmaja S Rao
(74) *Attorney, Agent, or Firm* — Gregory S. Darley-Emerson

(57) ABSTRACT

The present invention relates to a solid pharmaceutical preparation comprising α-lipoic acid, dicalcium phosphate and a binder. The solid pharmaceutical preparation has an improved stability and thereby improved bioavailability.

15 Claims, No Drawings

SOLID PHARMACEUTICAL PREPARATION CONTAINING LIPOIC ACID AND USE THEREOF

FIELD OF THE INVENTION

The present invention relates to a solid pharmaceutical preparation comprising α-lipoic acid, dicalcium phosphate and a binder. The solid pharmaceutical preparation has an improved stability and bioavailability. Further, the present invention relates to the use of and/or a method of use of the solid pharmaceutical preparation as disclosed herein for improvement of glucose transport and metabolism and/or protecting a body against free radical damages and/or oxidative stress. In addition or alternatively, the present invention relates to treatment of and/or a method of treatment of diabetic neuropathy.

BACKGROUND OF THE INVENTION

Lipoic acid (LA), also known as α-lipoic acid, alpha lipoic acid (ALA) and as thioctic acid, is a naturally occurring compound that is synthesized in small amounts by plants and animals, including humans. Endogenously synthesized lipoic acid is covalently bound to specific proteins, which function as cofactors for several important mitochondrial enzyme complexes such as, for example, those of pyruvate dehydrogenase, α-ketoglutarate dehydrogenase and of the branched-chain amino acids. In addition to the physiological functions of protein-bound lipoic acid, there is increasing scientific and medical interest in potential therapeutic uses of pharmacological doses of free lipoic acid. lipoic acid contains two thiol (sulfur) groups, which may be oxidized

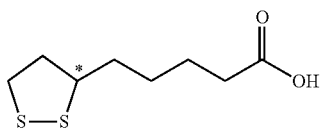 [SMILES: O=C(O)CCCCC1CCSS1]

or reduced

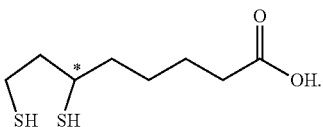 [SMILES: O=C(O)CCCCC(S)CCS]

The reduced form is known as dihydro α-lipoic acid (DHLA), while the oxidized form is known as LA.

Lipoic acid is a powerful antioxidant, a critical co-factor in ATP production, regulates lipid and carbohydrate metabolism. Lipoic acid (oxidized form) and dihydrolipoic acid (DHLA) (reduced form) are able to regenerate antioxidants including glutathione, ascorbic acid, and α-tocopherol (indirectly). Both LA acid and DHLA also protect the integrity of cell membranes by interacting with antioxidants-GSH, and vitamins E and C. Lipoic acid is found useful in the treatment of Diabetes II; it improves glucose transport and metabolism, diabetic neuropathy, cataracts, heavy metal poisoning, burning mouth syndrome, neurodegenerative disorders like Alzheimer's and Parkinson's disease. It also protects body against free radical damage and oxidative stress.

Lipoic acid occurs in different forms two enantiomers (R)-(+)-lipoic acid and (S)-(−)-lipoic acid. (R)-(+)-lipoic acid is the pure form found in nature from the simplest organisms up to the humans. Life does not exist without it, and it is found in every cell of the body. Lipoic acid consists of 50:50 racemic mixture of the R and S enantiomers and is the commonly commercially available form of lipoic acid.

Lipoic acid (oxidized) is labile to chemical degradation and gets converted into dihydrolipoic acid (DHLA), generating characteristic garlic like smell in formulation. Lipoic acid suffers from certain disadvantages, when it comes to developing a solid pharmaceutical dosage form such as tablets. In particular, it is very unstable to heat and light and is hygroscopic in nature. It has a low melting point of 60-61° C.; the natural form R-lipoic acid is unstable above 40° C. Lipoic acid undergoes a homolytic cleavage and is prone to form sticky gummy undesirable polymers, which causes problems in the manufacture of solid pharmaceutical dosage forms as well as in its release from such pharmaceutical dosage forms. For example, if compressed to tablets, lipoic acid can polymerize due to the heat generated during compression leading to capping problem in tablets, and partially polymerized product can cause significant stability problems for the dosage form. Further, the polymerization reduces dissolution, GI absorption and lowers the bioavailability of lipoic acid, since it is so poorly absorbed from the GI tract.

IN 1334MUM2010 proposes to tackle these problems by adding a combination of surfactant and antioxidant. Preferred surfactants used in IN 1334MUM2010 are a:b:a triblock co-polymers of ethylene oxide:propylene oxide:ethylene oxide such as Lutrol F127, antioxidants encompass for example, chelators, antioxidative vitamins, sulfites and others. In the examples surfactant Lutrol F127 is present versus lipoic acid in a weight ratio of 1 to 3. Such high amounts of surfactants are undesirable from the toxicological point of view, especially as lipoic acid is applied in dosages of up to 1000 mg. Further, as surfactants in a solid pharmaceutical preparation always require the presence of additional excipients such substantial amounts of surfactant requires further substantial additional amounts of excipients, which strongly increase the overall size of the administration form and its cost of goods. As the size of the solid oral dosage form is limited by its swallowability, the dose of lipoic acid to be applied with such a preparation is limited so that no high-dose solid pharmaceutical preparations can be provided.

It was an object of the present invention to provide a stable solid pharmaceutical preparation comprising lipoic acid that does not contain undesirable excipients such as surfactants. It was another object of the present invention to provide a stable solid pharmaceutical preparation that contains only minimal amounts of excipients which allows reduction of the size of the preparation and thereby facilitates its administration by the consumer. It was a further object of the present invention to provide a preparation that has a good dissolution and thereby provides a good bioavailability even after long storage times.

SUMMARY OF THE INVENTION

The present invention relates to a solid pharmaceutical preparation comprising lipoic acid as active agent, and a stabilizer comprising dicalcium phosphate and a binder.

The present invention further relates to a solid pharmaceutical preparation comprising lipoic acid as active agent in a safe and effective amount for improvement of glucose transport and metabolism and/or protecting a body against free radical damage and/or oxidative stress, together with a stabilizer comprising dicalcium phosphate and a binder.

The present invention further relates to a solid pharmaceutical preparation comprising lipoic acid as active agent in a safe and effective amount for treatment of Diabetes II, diabetic neuropathy, cataracts, heavy metal poisoning, burning mouth syndrome, neurodegenerative disorders, Alzheimer's and Parkinson's disease, together with a stabilizer comprising dicalcium phosphate and a binder; in a preferred embodiment the present invention relates to said solid pharmaceutical preparation for treatment of diabetic neuropathy.

The present invention further relates to a method for preparing the solid pharmaceutical preparation comprising lipoic acid as active agent, and a stabilizer comprising dicalcium phosphate and a binder, wherein the preparation is a granulate. In one embodiment the method comprises dry- or wet-granulation.

In one embodiment the present invention further relates to a pharmaceutical preparation comprising (±) lipoic acid as active agent; a stabilizer comprising dicalcium phosphate and a vinylpyrrolidone-vinyl acetate copolymer, wherein the weight ratio from lipoic acid to dicalcium phosphate is about 2:1 and the weight ratio from lipoic acid to the binder is about 1:0.05; vitamin B1, vitamin B6 and vitamin B12, wherein the vitamin B1, vitamin B6 and vitamin B12 are present in relation to each other in a weight ratio of 2:1:2; and a pharmaceutically acceptable excipient comprising from 40 to 45% of a filler, and from 1 to 5% (w/w) of each of a disintegrant, of a glidant and of a lubricant.

The present invention further relates to a method of treatment of Diabetes II, diabetic neuropathy, cataracts, heavy metal poisoning, burning mouth syndrome, neurodegenerative disorders, Alzheimer's and/or Parkinson's disease, by administering to an individual in need of this treatment a safe and effective amount of lipoic acid together with a stabilizer comprising dicalcium phosphate and a binder. In one embodiment the present invention relates to a method of treatment of diabetic neuropathy by administering to an individual in need of this treatment a safe and effective amount of lipoic acid together with a stabilizer comprising dicalcium phosphate and a binder.

The present invention further relates to a method of improving glucose transport and metabolism and/or protecting a body against free radical damage and/or oxidative stress, by administering to an individual in need of this improvement and/or protection a safe and effective amount of lipoic acid together with a stabilizer comprising dicalcium phosphate and a binder.

The present invention further relates to a kit comprising the solid preparation as disclosed herein comprising lipoic acid in a safe and effective amount as active agent, and a stabilizer comprising dicalcium phosphate and a binder together with instructions to use.

DETAILED DESCRIPTION OF THE INVENTION

While the specification concludes with claims particularly pointing out and distinctly claiming the invention, it is believed that the present invention will be understood better from the following description of embodiments.

By "g" as used herein is meant grams; by "mg" as used herein is meant milligrams. By "min" as used herein is meant minutes.

The term "w/w" and "weight %" as used herein means percentage by weight and generally all percentages and ratios used herein after are by weight of total preparation unless otherwise indicated.

All percentages, ratios, levels and concentration of ingredients referred to herein are based on the actual amount of the ingredient, and do not comprise solvents, fillers, or other materials with which the ingredient may be combined as a commercially available product, unless otherwise indicated.

All measurements referred to herein are made at about 22° C. (i.e. room temperature) unless otherwise specified.

As used herein, "about" refers to a numeric value, including, for example, whole numbers, fractions, and percentages, whether or not explicitly indicated. The term "about" generally refers to a range of numerical values (e.g., +/−1-3% of the recited value) that one of ordinary skill in the art would consider equivalent to the recited value (e.g., having the same function or result). In some instances, the term "about" may include numerical values that are rounded to the nearest significant figure.

As used herein, the word "or" when used as a connector of two or more elements is meant to include the elements individually and in combination; for example, X or Y, means X or Y or both.

As used herein, the articles "a" and "an" are understood to mean one or more of the materials that is claimed or described, for example, "an active" or "a solvent". As used herein "another" means at least a second or more. Furthermore, unless otherwise required by context, singular terms include pluralities and plural terms include the singular.

As used herein, the word "comprise," and its variants, are intended to be non-limiting, such that recitation of items in a list is not to the exclusion of other like items that may also be useful in the materials, preparations, kits, and methods of this invention. This term encompasses the terms "consisting of" and "consisting essentially of".

As used herein, the word "include," and its variants, are intended to be non-limiting, such that recitation of items in a list is not to the exclusion of other like items that may also be useful in the materials, preparations, kits, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful and it is not intended to exclude other embodiments from the scope of the invention.

"Active", "active agent" and "active ingredients" useful herein may be categorized or described herein by their therapeutic benefit or their postulated mode of action or function. However, it is to be understood that the actives and other ingredients useful herein can, in some instances, provide more than one therapeutic benefit or function or operate via more than one mode of action. Therefore, classifications herein are made for the sake of convenience and are not intended to limit an ingredient to the particularly stated function(s) or activities listed.

By "safe and effective amount" as used herein is meant an amount of a component, high enough to significantly (positively) modify the condition to be treated or to affect the desired result, but low enough to avoid serious side effects (at a reasonable benefit/risk ratio), within the scope of sound medical judgment. The safe and effective amount of a component will vary with the condition being treated, the age and physical condition of the patient being treated, the severity of the condition, the duration of treatment, the nature of concurrent therapy, the specific form employed, and the particular vehicle from which the component is applied.

As used herein, the terms "administer," "administering," and "administration," refer to any method which, in sound medical practice, delivers the preparation to a subject in such a manner as to provide a therapeutic effect.

As used herein, "medication" refers to medications, such as pharmaceuticals, including prescription medications, over-the-counter medications, behind-the-counter medications and combinations thereof. In some examples, a medication can be a supplement.

Surprisingly, it has been found that a solid pharmaceutical preparation which meets these requirements and has an improved storage stability can be provided if it comprises besides lipoic acid as active agent a stabilizer comprising dicalcium phosphate and a binder.

The active agent lipoic acid, herein also abbreviated as ALA, can be present as (R)-(+)-lipoic acid, (S)-(−)-lipoic acid and/or as a racemic mixture (±)-lipoic acid. In a preferred embodiment lipoic acid is present as racemic mixture. Accordingly, one embodiment of the present invention is also directed to a solid pharmaceutical preparation, wherein lipoic acid is racemic (±)-lipoic acid.

The stabilizer comprises dicalcium phosphate and a binder. Dicalcium phosphate ($CaHPO_4$) can be present as dihydrate ($CaHPO_4 \cdot 2H_2O$), hemihydrate ($CaHPO_4 \cdot H_2O$) or in anhydrous form ($CaHPO_4$). In a preferred embodiment dicalcium phosphate is present in its anhydrous form. Therefore, one embodiment of the present invention is further directed to a solid pharmaceutical preparation, wherein the dicalcium phosphate is anhydrous dicalcium phosphate.

Surprisingly, only a small amount of dicalcium phosphate (relative to ALA) is sufficient to provide a solid pharmaceutical preparation that is stable and has a good dissolution even after long storage times. Beside a binder, no further excipient is needed to improve said stability and good dissolution even after long storage times. In an appropriate embodiment of the present invention lipoic acid and dicalcium phosphate are present in relation to each other in a weight ratio from about 1:1 to about 10:1, preferably from about 1.5:1 to about 7:1, more preferably from about 1.5:1 to about 3:1, and most preferably in a weight ratio from 1.6:1 to 2:1. Accordingly, one embodiment of the present invention is further directed to a solid pharmaceutical preparation, wherein lipoic acid and dicalcium phosphate are present in relation to each other in a weight ratio from about 1:1 to about 10:1, preferably from about 1.5:1 to about 7:1, more preferably from about 1.5:1 to about 3:1, and most preferably in a weight ratio from 1.6:1 to 2:1.

In addition, a binder is present as an adjuvant for the production of solid pharmaceutical preparation as disclosed herein to provide cohesion of the solid pharmaceutical preparation. Appropriate binders which can be employed in the present invention are, for example, one or more of polyvinylpyrrolidone, polyvinyl acetate, a vinylpyrrolidone-vinyl acetate copolymer, a starch paste, such as maize starch paste, a cellulose derivative, such as hydroxypropyl methylcellulose or hydroxypropyl cellulose. Therefore, one embodiment of the present invention is as well directed to a solid pharmaceutical preparation, wherein the binder is one or more of polyvinylpyrrolidone, polyvinyl acetate, a vinylpyrrolidone-vinyl acetate copolymer, a starch paste, such as maize starch paste, a cellulose derivative, such as hydroxypropyl methylcellulose or hydroxypropyl cellulose.

In a preferred embodiment the binder present in the solid pharmaceutical preparation as disclosed herein is polyvinylpyrrolidone, polyvinyl acetate, a vinylpyrrolidone-vinyl acetate copolymer and/or hydroxypropyl cellulose. In another preferred embodiment the binder present in the solid pharmaceutical preparation as disclosed herein is a vinylpyrrolidone-vinyl acetate copolymer or a combination of a vinylpyrrolidone-vinyl acetate copolymer and hydroxypropyl cellulose. Thus, one embodiment of the present invention is also directed to a solid pharmaceutical preparation, wherein the binder is a vinylpyrrolidone-vinyl acetate copolymer or a combination of a vinylpyrrolidone-vinyl acetate copolymer and hydroxypropyl cellulose.

The term "hydroxypropyl cellulose" as used herein refers to a hydroxypropyl cellulose, wherein the content of hydroxypropyl group in the hydroxypropyl cellulose (hereinafter, also abbreviated to "the content of HPC group") is from 20 to 90 weight %, preferably from 40 to 85 weight %, more preferably from 53.4 to 80.5 weight %. The content of a hydroxypropyl group can be determined by a method described in a section of hydroxypropyl cellulose" in the European Pharmacopoeia (Ph. Eur. 9.0).

The term "vinylpyrrolidone-vinyl acetate copolymer" as used herein refers to a water soluble polymer made from the copolymerization of vinylpyrrolidone with vinyl acetate. Vinylpyrrolidone-vinyl acetate copolymer is referenced in European and US pharmacopeia (Ph. Eur. and USP) as Copovidone.

In an appropriate embodiment of the present invention lipoic acid and the binder are present in relation to each other in a weight ratio from about 1:0.1 to about 1:0.01, preferably in a weight ratio from about 1:0.1 to about 1:0.02, more preferably in a weight ratio from about 1:0.08 to about 1:0.03, and most preferably in a weight ratio from about 1:0.05. Accordingly, one embodiment of the present invention is further directed to a solid pharmaceutical preparation, wherein lipoic acid and the binder are present in relation to each other in a weight ratio from about 1:0.1 to about 1:0.01, preferably from about 1:0.11 to about 1:0.02, more preferably from about 1:0.08 to about 1:0.03, and most preferably in a weight ratio from about 1:0.05.

The stability and storage properties of the present solid preparation as disclosed herein are achieved by the combination of dicalcium phosphate and the binder. In an appropriate embodiment of the present invention dicalcium phosphate and the binder are present in relation to each other in a weight ratio from about 2:1 to about 1:0.01, preferably in a weight ratio from about 1:1 to about 1:0.05, more preferably in a weight ratio from about 1:0.5 to about 1:0.07, and most preferably in a weight ratio from about 1:0.1. Accordingly, one embodiment of the present invention is further directed to a solid pharmaceutical preparation, wherein dicalcium phosphate and the binder are present in relation to each other in a weight ratio from about 2:1 to about 1:0.01, preferably from about 1:1 to about 1:0.05, more preferably from about 1:0.0 to about 1:0.07, and most preferably in a weight ratio from about 1:0.1.

The solid pharmaceutical preparation as disclosed herein can be in granule, pellet, capsule or tablet form. While capsules, tablets and suppositories provide the amount of active compound intended to be taken in each case as a clearly defined individual dose, the amount of active compound required in each case can be adapted in a simple manner by means of pellets and granules. In a preferred embodiment the solid pharmaceutical preparation as disclosed herein is in tablet form.

Suppositories are solid, single-dose preparation prepared by compression or moulding or any other technique well known from the skilled artisan, that contains one or more active substances dispersed or dissolved in a suitable basis which may be soluble or dispersible in water or may melt at body temperature, and optionally excipients.

Granules are flowable granular aggregates of powders which can be prepared by granulation. Pellets are solid, small, spherical medicament forms, such as, for example, granule grains or microtablets, having a very narrow particle-size range. Pellets can be produced by granulation and subsequent rounding-off (spheronisation), for example by means of plate granulation, or alternatively by pressing powders or granules to give microtablets.

Granules and pellets represent an independent medicament form, but can also serve as intermediate product for the production of tablets. If it is intended that predetermined amounts of active compound can be administered by means of granules or pellets, these are, in order to ensure adequate dosage accuracy, also provided as portioned granules or introduced into capsules. The solid pharmaceutical preparation according to the invention is preferably in granule, pellet, capsule, suppository or tablet form, particular preferably in capsule or tablet form, very particular preferably in tablet form.

Therefore, a further embodiment of the present invention is directed to a solid pharmaceutical preparation, which is in granule, pellet, capsule, suppository or tablet form, particular preferably in capsule or tablet form. A very particularly preferred embodiment of the present invention is directed to a solid pharmaceutical preparation as disclosed herein, which is a tablet.

According to an appropriate embodiment of the present invention the solid pharmaceutical preparation is a tablet further optionally comprising one or more pharmaceutically acceptable excipient selected from the group consisting of a filler, a disintegrant, a glidant and a lubricant.

The term "filler" as used herein is an agent increasing the bulk of the pharmaceutical preparation by providing the quantity of material which is needed to form such pharmaceutical preparation. A filler also serves to create desired flow properties and compression characteristics in the preparation of tablets and capsule fillers. Fillers usable in the present invention may be a sugar alcohol such as sorbitol or mannitol, dulcitol, xylitol or ribitol, preferably sorbitol or mannitol, particular preferably mannitol, a sugar such as glucose, fructose, mannose, lactose, saccharose or maltose, preferably lactose, saccharose or maltose, particular preferably lactose, a starch such as potato starch, rice starch, maize starch or pregelatinized starch, preferably maize starch or pregelatinized starch, particular preferably maize starch, a cellulose such as powdered cellulose or microcrystalline cellulose, preferably microcrystalline cellulose, or a mixture thereof. In a particularly preferred embodiment of the invention the pharmaceutical preparation comprises microcrystalline cellulose as filler. Fillers are present in the pharmaceutical preparation according to one embodiment of the invention in a proportion of 0 to about 55% (w/w), preferably from about 20% to about 50% (w/w), particularly preferably from about 30% to 48% (w/w), more preferably from about 40% to about 45% (w/w).

The term "disintegrant" as used herein refers to a compound that expands and dissolves when wet, to cause disintegration of tablets or granulates to break apart and release the active pharmaceutical agent. The disintegrant also functions to ensure that the compounds are in contact with the solvent, such as water. Disintegrants serve to disintegrate tablets or granules etc. and thus enhance dissolution of the solid dosage form upon contact with the liquid dissolution medium. Suitable disintegrants include crospovidone (cross linked polyvinyl N-pyrrolidone), low-substituted hydroxypropyl cellulose, carboxymethylcellulose and salts and derivatives thereof, such as crosslinked derivatives, for instance croscarmellose sodium (crosslinked polymer of carboxymethylcellulose sodium,) sodium carboxymethyl glycolate, sodium starch glycolate, carrageenan, agar, and pectin. Crospovidone, low-substituted hydroxypropyl cellulose and croscarmellose sodium are particularly preferred. Disintegrants are present in the pharmaceutical preparation according to the invention in a proportion of 0 to about 20% (w/w), preferably from about 0.1% to about 15% (w/w), particularly preferably from about 0.5% to about 10% (w/w), most preferably from about 1% to about 5% (w/w).

The term "low-substituted hydroxypropyl cellulose" as used herein refers to a low-substituted hydroxypropyl cellulose wherein the content of hydroxypropyl group in the hydroxypropyl cellulose (hereinafter, also abbreviated to "the content of HPC group") is about 5.0 to 9.9 weight %. The content of a hydroxypropyl group can be determined by a method described in a section of "low-substituted hydroxypropyl cellulose" in the European Pharmacopoeia (Ph. Eur. 9.0). Low-substituted hydroxypropyl cellulose are, for example, LH-22, LH-32, which have a content of HPC group of about 5.0 to 7.0 weight %, or LH-23, LH-33, which have a content of HPC group of about 7.0 to 9.9 weight %.

The term "lubricant" as used herein refers to an inactive ingredient used to prevent sticking of ingredients to one another in capsule filling or tablet compressing machines. A lubricant reduces the sliding friction of the tableting material and ram in the mould during the tableting operation and to prevent sticking to the rams. Suitable lubricants are alkaline-earth metal salts of fatty acids, such as magnesium stearate or calcium stearate, fatty acids, such as stearic acid, higher fatty alcohols such as cetyl alcohol or stearyl alcohol, fats such as glyceryl dipalmitostearate, glyceryl distearate, stearin or glyceryl dibehenate, alkaline-earth metal salts of C16-C18 alkyl substituted dicarbonic acids such as sodium stearyl fumarate, hydrated vegetable oils such as hydrated castor oil or hydrated cotton seed oil, or minerals such as talc. Preferred lubricants are magnesium stearate, stearic acid or sodium stearyl fumarate as lubricant, particular preferred is magnesium stearate. Lubricants are present in the pharmaceutical preparation according to the invention in a proportion of 0 to about 5% (w/w), preferably about 0.1% to about 3% (w/w), particularly preferably about 0.5% to about 2.5% (w/w), most preferably about 2.0% (w/w).

The term "glidant" as used herein refers to an inactive ingredient used as a flow aid that improves the flow characteristics of particulates such as powders or granules. In the present invention flow characteristics of the composite or the mixtures containing the composite during further processing such as encapsulation or tableting. Nonlimiting examples of glidants for use in the present invention include colloidal silicon dioxide (Aerosil 200, Cab-O-Sil), talc, magnesium carbonate, and combinations thereof. Glidants are present in the pharmaceutical preparation according to the invention in a proportion of 0 to about 7.5% (w/w), preferably about 0.1% to about 5% (w/w), particularly preferably about 0.5% to about 4% (w/w), most preferably about 3% (w/w).

According to an appropriate embodiment of the present invention the solid pharmaceutical preparation is a tablet comprising 25 to 100% (w/w), preferably 30 to 80% (w/w), more preferably 35 to 70% (w/w) of the pharmaceutically acceptable excipient comprising 0 to 55% (w/w) of a filler, 0 to 20% (w/w) of disintegrant, 0 to 5% (w/w) of a lubricant 0 to 7.5% (w/w) of glidant, based upon the total weight of the tablet, preferably the pharmaceutically acceptable excipient further comprises a total of 0 to 20% (w/w), preferably 0.1 to 20% (w/w) of one or more additional pharmaceutically acceptable excipients, based upon the total weight of the tablet.

The solid pharmaceutical preparation may comprise, besides lipoic acid, one or more further active ingredients such as vitamins, preferably water-soluble vitamins, more preferably B vitamins, most preferably vitamin B1, vitamin B6 and/or vitamin B12. Therefore, the present invention is also directed to a solid pharmaceutical preparation, further comprising one or more vitamins, preferably one or more water-soluble vitamins, more preferably one or more B vitamins, most preferably vitamin B1, vitamin B6 and/or vitamin B12. Presence of B vitamins is of particular value if the preparation is intended to be used for the prophylaxis or treatment of neural disorders such as diabetic peripheral neuropathy.

In an appropriate embodiment of the present invention the lipoic acid and the one or more vitamins are present in relation to each other in a weight ratio from about 1:0.01 to about 1:1, preferably in a weight ratio from about 1:0.1 to about 1:0.5, more preferably in a weight ratio from about 1:0.2 to about 1:0.3. Accordingly, one embodiment of the present invention is further directed to a solid pharmaceutical preparation, wherein the lipoic acid and the one or more vitamins are present in relation to each other in a weight ratio from about 1:0.01 to about 1:1, preferably from about 1:0.1 to about 1:0.5, more preferably from about 1:0.2 to about 1:0.3.

If the solid pharmaceutical preparation is a granulate it can be prepared by dry-granulation or wet-granulation, preferably wet-granulation. Thus, one embodiment of the invention is also directed to a method for preparing a solid pharmaceutical preparation, which is a granulate, the method comprising dry-granulation or wet-granulation, preferably wet-granulation.

Granulation refers to a process of forming granules through blending and intimate mixing of drug substances and pharmaceutical additives and an input of energy. The term "wet-granulation" refers to a process of forming granules from a blend of active ingredients and pharmaceutically acceptable excipients with the help of water or solvents. The term "dry-granulation" refers to a process of forming granules from active ingredients and pharmaceutically acceptable excipients with the help of pressure.

In the case of wet-granulation, for example, a granulation liquid, which preferably comprises a binder, is added to a powder mixture comprising the active compound together with an excipient and any further suitable adjuvants, the mixture is converted into aggregates of suitable size (granules) and subsequently dried. The active compound can also be introduced into the granules by suspension in the granulation liquid. The conversion of the powder mixture into aggregates of suitable size can be carried out, for example, by so-called build-up granulation, for example in coating pans, by means of plate granulation or in fluidised-bed processor, for example by the Glatt or Wurster method, or by so-called reduction granulation, in which the powder mixture is firstly wetted and converted into a plastically mouldable mass and subsequently converted into aggregates of desired size, for example by extrusion through a screen having meshes of suitable size.

In the case of dry-granulation, the powder mixture is pressed, for example, by means of compaction between two counter-rotating compaction rolls to give flakes, which are subsequently milled to give granules, e.g. by crushing, grinding or cutting into dry granulated particles, the granulate. Optionally, the granulate may be further processed. Crushing, grinding, or cutting processes involve an operation that reduces the size of the compressed material such as accomplished by milling or by other operations known to those skilled in the art.

According to a preferred embodiment, the method for preparing the granulate comprises the steps (a) dissolving the binder, and optionally one or more pharmaceutically acceptable excipient in a solvent; (b) spraying the solution obtained by step (a) onto the lipoic acid and dicalcium phosphate in a fluidized bed granulation and drying to form granules; and (c) collecting the granules obtained by step (b). Thus, the present invention is also directed to a method for preparing the granulate, the method comprising the steps: (a) dissolving the binder, and optionally one or more pharmaceutically acceptable excipient in a solvent; (b) spraying the solution obtained by step (a) onto the lipoic acid and dicalcium phosphate in a fluidized bed granulation and drying to form granules; and (c) collecting the granules obtained by step (b).

According to a further preferred embodiment, the method for preparing the granulate comprises the steps (a) mixing the binder, dicalcium phosphate and lipoic acid; (b) spraying a solvent onto the mixture obtained in step a in a fluidized bed granulation and drying to form granules; and (c) collecting the granules obtained by step (b). Thus, the present invention is also directed to a method for preparing the granulate, the method comprising the steps: (a) mixing the binder, dicalcium phosphate and lipoic acid; (b) spraying a solvent onto the mixture obtained in step a in a fluidized bed granulation and drying to form granules; and (c) collecting the granules obtained by step (b).

In addition, to a further preferred embodiment the present invention refers to the method for preparing the pharmaceutical preparation, which is a tablet, the method comprising the steps: (a) mixing the granules obtained by the method steps as disclosed above with a disintegrant and optionally a lubricant and/or one or more further excipient; (b) compressing the mixture obtained by step (a) to give tablets; and (c) optionally film coating of the tablets prepared by step (b). Thus, the present invention is also directed to a method for preparing the pharmaceutical preparation, which is a tablet, the method comprising the steps: (a) mixing the granules obtained by the method as disclosed above with a disintegrant and optionally a lubricant and/or one or more further excipient; (b) compressing the mixture obtained by step (a) to give tablets; and (c) optionally film coating of the tablets prepared by step (b).

Lipoic acid and the stable solid pharmaceutical preparation as disclosed herein can be used to any physiological and medical treatment and indication lipoic acid is known for. In one embodiment the Lipoic acid and the stable solid pharmaceutical preparation as disclosed herein are used for improvement of glucose transport and metabolism, which may be in particular helpful in treatment of Diabetes II, in particular diabetic neuropathy. Further, lipoic acid and the stable solid pharmaceutical preparation as disclosed herein are intended to be used for protecting a body against free radical damage and/or oxidative stress. Other suitable medical use may be for heavy metal poisoning, burning mouth syndrome, neurodegenerative disorders, Alzheimer's or Parkinson's disease.

The pharmaceutical preparation as disclosed herein may be administered internally, in particular orally. Dosage forms that can be orally administered, such as tablets, may be swallowed immediately, slowly dissolved in the mouth, or chewed. Internal application requires application of the pharmaceutic composition in a dose to achieve and effect, wherein the effect remains for a sufficient period of time. By "dose" as used herein is meant a volume of medication, containing an amount of a drug active suitable for administration on a single occasion, according to sound medical practice. A dose can be orally administered. In one example, a dose can be half of a tablet or capsule, in another example one tablet or capsule, in another embodiment 1.5 tablets or capsules, in another embodiment 2 tablets or capsules, in another embodiment 2.5 tablets or capsules, and in another embodiment 3 tablets or capsules. The concentration of active ingredients can be adjusted to provide the proper doses of actives given the dose size. In a preferred embodiment a dose of solid medication may be about 600 mg per day. In another embodiment a dose may be from 600 mg to 1800 mg per day. In one example, the dose is intended to be administered once a day.

The present invention relates further to a kit comprising the solid pharmaceutical preparation as disclosed herein comprising at least lipoic acid in a safe and effective amount and a stabilizer comprising dicalcium phosphate and a binder as well as instructions to use. The using instruction will describe some example application scenarios as described herein, but the optimal amount, duration and frequency of application will depend on the desired effect, the severity of any condition being treated, the health and age of the user and like considerations.

Further preferred embodiments are based on the dependent patent claims. Features of the solid pharmaceutical preparation claims can be combined correspondingly with the use claims and vice versa in any desired combination.

In the following the present invention will be described in further detail by examples. The examples illustrate the invention without being restricted thereto.

EXAMPLES

Analytical Test Methods:

Assay and Dissolution of the solid composition comprising lipoic acid are tested by high-performance liquid chromatography with UV detection using a stability indicating method. We use purified water as the dissolution medium. Dissolution is a good test to monitor the stability of ALA as polymerized form of ALA has poor solubility in purified water.

EXAMPLE COMPOSITIONS

Example 1

Granules Comprising
600 mg of lipoic acid (±)-Lipoic acid
60 mg low-substituted hydroxypropyl cellulose
200 mg of anhydrous calcium phosphate
60 mg of hydroxypropylcellulose (HPC)

The granules are produced by granulation of the active compound with low-substituted hydroxypropyl cellulose and an aqueous solution of anhydrous calcium phosphate and HPC in the fluidized bed.

Example 2

Tablet comprising
600 mg of lipoic acid (±)-Lipoic acid
200 mg of anhydrous dicalcium phosphate
60 mg of hydroxypropylmethylcellulose
35 mg of croscarmellose sodium
35 mg of highly disperse silicon dioxide
20 mg of magnesium stearate Granules produced as described in Example 1 are admixed with croscarmellose sodium, silicon dioxide and magnesium stearate, the resultant mixture is pressed to give tablets of Example 2.

The tablets are transferred into HDPE bottles, stored under 30° C./75% RH for predetermined times and subsequently investigated with respect to active-compound content, dissolution and disintegration. Storage times (in months), dissolution and disintegration times measured in each case are shown in Table 1.

TABLE 1

| Evaluation parameters | Specifications | Initial | 1 M | 2 M | 3 M | 6 M |
|---|---|---|---|---|---|---|
| Dissolution | Not less than 70% API release in 60 min | 91 | 88 | 89 | 90 | 83 |
| Assay | As per guidelines stated by United States Pharmacopeia (USP) | 99.9 | 100.1 | 98.7 | 100.2 | 99.9 |
| Disintegration | Not more than 30 min for Film coated tablets Guidelines stated by USP | 2-3 min | 2-3 min | 2-3 min | 2-3 min | 4-5 min |

Example 3

Granules Comprising
600 mg of lipoic acid (±)-Lipoic acid
120 mg of anhydrous calcium phosphate
25 mg of PVP-VA The granules are produced by granulation of the active compound and an aqueous solution of anhydrous calcium phosphate and PVP-VA in the fluidized bed.

Example 4

Tablet comprising
600 mg of lipoic acid (±)-Lipoic acid
235 mg of anhydrous dicalcium phosphate
25 mg of PVP-VA
35 mg of croscarmellose sodium
25 mg of highly disperse silicon dioxide
20 mg of magnesium stearate Granules produced as described in Example 3 are admixed with croscarmellose sodium, silicon dioxide and magnesium stearate, the resultant mixture is pressed to give tablets of Example 4.

The tablets are transferred into HDPE bottles, stored under 30° C./75% RH for predetermined times and subsequently investigated with respect to active-compound content, dissolution and disintegration. Storage times (in months), dissolution and disintegration times measured in each case are shown in Table 2.

TABLE 2

| CQA | Specifications | Initial | 1 M | 2 M | 3 M | 6 M |
| --- | --- | --- | --- | --- | --- | --- |
| Dissolution | Not less than 70% API release in 60 min | 91 | 96 | 90 | 89 | 93 |
| Assay | As per guidelines stated by United States Pharmacopeia (USP) | 98.8 | 100.8 | 99 | 98.7 | 99.6 |
| Disintegration | Not more than 30 min for Film coated tablets Guidelines stated by USP | 1-2 min | 1-2 min | 1-2 min | 1-2 min | 1-2 min |

Example 5

Granules comprising
600 mg of lipoic acid (+)-Lipoic acid
200 mg of anhydrous dicalcium phosphate
60 mg low substituted hydroxypropyl cellulose
60 mg of hydroxypropyl cellulose The granules are produced by granulation of the active compound and an aqueous solution of anhydrous calcium phosphate, PVP-VA and hydroxypropyl cellulose in the fluidized bed.

Example 6

Tablet comprising
600 mg of lipoic acid (±)-Lipoic acid
250 mg of anhydrous dicalcium phosphate
60 mg low-substituted hydroxypropyl cellulose
60 mg hydroxypropyl cellulose (HPC)
98.25 mg microcrystalline cellulose (MCC)
50.75 mg of croscarmellose sodium
14.5 mg of highly dispersed silicon dioxide
29 mg of magnesium stearate
100 mg Vitamin B1
50 mg Vitamin B6
100 mg Vitamin B12 (as 1% triturate)

Vitamin B1 and Vitamin B6 are admixed and granulated in an aqueous solution of HPMC in the fluidized bed. Blend of such granules with granules produced as described in Example 1 is blended with Vitamin B12, admixed with MC, croscarmellose sodium, silicon dioxide and magnesium stearate, the resultant mixture is pressed to give tablets.

The tablets are transferred into HDPE bottles, stored under 30° C./75% RH for predetermined times and subsequently investigated with respect to active-compound content, dissolution and disintegration. Storage times (in months), dissolution and disintegration times measured in each case are shown in Table 3.

TABLE 3

| Evaluation Parameters | Specifications | Actives | Initial | 1 M | 3 M | 6 M |
| --- | --- | --- | --- | --- | --- | --- |
| Dissolution | Not less than 70% API release in 60 min | ALA | 90 | 88 | 87 | 72 |
| | Not less than 80% API release in 45 min | B1 | 95 | 95 | 97 | 97 |
| | | B6 | 98 | 98 | 100 | 99 |
| | | B12 | 101 | 97 | 98 | 102 |

TABLE 3-continued

| Evaluation Parameters | Specifications | Actives | Initial | 1 M | 3 M | 6 M |
| --- | --- | --- | --- | --- | --- | --- |
| Assay | As per guidelines stated by USP | ALA | 97.8 | 100.3 | 98.3 | 97.6 |
| | | B1 | 97.2 | 96.8 | 97 | 96.4 |
| | | B6 | 99.9 | 99.9 | 99.8 | 98.8 |
| | | B12 | 105.7 | 105.2 | 101 | 104.5 |

Example 7

Granules comprising
600 mg of lipoic acid (±)-Lipoic acid
270 mg of anhydrous dicalcium phosphate
25 mg of PVP-VA The granules are produced by granulation of the active compound and an aqueous solution of anhydrous calcium phosphate and PVP-VA in the fluidized bed.

Example 8

Tablet comprising
600 mg of lipoic acid (±)-Lipoic acid
60 mg low-substituted hydroxypropyl cellulose
270 mg of anhydrous dicalcium phosphate
25 mg of PVP-VA
120 mg microcrystalline cellulose (MCC)
43.5 mg of croscarmellose sodium
36.25 mg of highly dispersed silicon dioxide
30 mg of magnesium stearate
100 mg Vitamin B1
50 mg Vitamin B6
100 mg Vitamin B12 (as 1% triturate)

Vitamin B1 and Vitamin B6 are admixed and granulated in an aqueous solution of HPMC in the fluidized bed. Blend of such granules with granules produced as described in Example 7 is blended with Vitamin B12, admixed with microcrystalline cellulose, croscarmellose sodium, highly dispersed silicon dioxide, and magnesium stearate. The resultant mixture is pressed to give tablets of Example 8.

The tablets of Example 8 are transferred into HDPE bottles, stored under 30° C./75% RH for predetermined times and subsequently investigated with respect to active-compound content, dissolution and disintegration. Storage times (in months), dissolution and disintegration times measured in each case are shown in Table 4.

TABLE 4

| Evaluation Parameters | Specifications | Actives | Initial | 1 M | 3 M | 6 M |
|---|---|---|---|---|---|---|
| Dissolution | Not less than 70% API release in 60 min | ALA | 89 | 91 | 88 | 86 |
| | Not less than 80% API release in 45 min | B1 | 99 | 100 | 100 | 97 |
| | | B6 | 90 | 92 | 91 | 87 |
| | | B12 | 102 | 101 | 95 | 101 |
| Assay | As per guidelines stated by United States Pharmacopeia (USP) | ALA | 96.9 | 97.3 | 97 | 96.5 |
| | | B1 | 98.1 | 100.3 | 102.6 | 97.4 |
| | | B6 | 89.5 | 91.7 | 93.7 | 88.5 |
| | | B12 | 105.7 | 105.3 | 101.2 | 103.4 |

In addition or alternatively, the granules as prepared in Example 1, 3, 5 and/or 7 are mixed with magnesium stearate as lubricant and transferred and filled into empty hard gelatine capsules.

COMPARATIVE EXAMPLES

In comparative examples granules and tablets are prepared that comprise excipients that are known in the art to stabilize lipoic acid (see, for example, Technical Newsletter/December 2008 from Fuji Chemical Industry relating to Neusilin®, a synthetic, amorphous form of magnesium aluminometasilicate).

Comparative Example 1

Granules comprising
600 mg of lipoic acid (±)-Lipoic acid
160 mg of stabilizer 1 (Florite R)
40 mg of stabilizer 2 (Neusilin®)
A blend of active active-compound, stabilizer 1 (silicate) and stabilizer 2 (Neusilin) are compressed by a roller compactor into slugs and broken to provide granules.

Comparative Example 2

Tablet comprising
600 mg of lipoic acid (±)-Lipoic acid
160 mg of stabilizer 1 (silicate)
40 mg of stabilizer 2 (Neusilin®)
40 mg of diluent (MCC)
20 mg of croscarmellose sodium
20 mg of highly disperse silicon dioxide
30 mg of magnesium stearate
Granules produced as described in Comparative Example 1 are admixed with croscarmellose sodium, silicon dioxide and magnesium stearate, the resultant mixture is pressed to give tablets of Comparative Example 2.

Comparative Example 3

Granules comprising
600 mg of lipoic acid (±)-Lipoic acid
180 mg of stabilizer 1 (Florite R)
A blend of active active-compound and stabilizer 1 (silicate) are compressed by a roller compactor into slugs and broken to provide granules.

Comparative Example 4

Tablet comprising
600 mg of lipoic acid (±)-Lipoic acid
180 mg of stabilizer 1 (silicate)
50 mg of diluent (MCC)
30 mg of croscarmellose-Na
30 mg of highly disperse silicon dioxide
30 mg of magnesium stearate
Granules produced as described in Comparative Example 3 are admixed with croscarmellose sodium, silicon dioxide and magnesium stearate, the resultant mixture is pressed to give tablets of Comparative Example 4. The tablets are transferred into HDPE bottles, stored under 30° C./75% RH for predetermined times and subsequently investigated with respect to active-compound content, dissolution and disintegration. Storage times (in months), dissolution and disintegration times measured in each case are shown in Table 5.

TABLE 5

| Product tested | Evaluation parameters | Specification | Initial | 1 M | 2 M | 3 M | 6 M |
|---|---|---|---|---|---|---|---|
| Comp. Ex.2 | Dissolution | Not less than 70% API release in 60 min | 87 | 58 | 46 | not dissolved | NA |
| | Assay | As per guidelines stated by USP | 96.9 | 93.7 | 94.2 | NA | NA |
| | Disintegration | Not more than 30 min for Film coated tablets Guidelines stated by USP | 2-3 min | 5-6 min | not disintegrated | not disintegrated | NA |
| Comp. Ex.4 | Dissolution | | 88 | 61 | 44 | not dissolved | NA |
| | Assay | As per guidelines stated by USP | 96.1 | 94.2 | 94.3 | NA | NA |

TABLE 5-continued

| Product tested | Evaluation parameters | Specification | Initial | 1 M | 2 M | 3 M | 6 M |
|---|---|---|---|---|---|---|---|
| | Disintegration | Not more than 30 min for Film coated tablets Guidelines stated by USP | 3-5 min | 7-8 min | NA | NA | NA |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A solid pharmaceutical preparation comprising (i) a safe and effective amount of lipoic acid as active agent, (ii) a stabilizer comprising dicalcium phosphate, (iii) a binder comprising a vinylpyrrolidone-vinyl acetate copolymer, wherein the lipoic acid and the binder are present in relation to each other in a weight ratio of from about 1:0.08 to about 1:0.03.

2. The solid pharmaceutical preparation according to claim 1, wherein lipoic acid is racemic (±) lipoic acid.

3. The solid pharmaceutical preparation according to claim 1, wherein lipoic acid and dicalcium phosphate are present in relation to each other in a weight ratio from about 1:1 to about 10:1.

4. The solid pharmaceutical preparation according to claim 1, wherein lipoic acid and dicalcium phosphate are present in relation to each other in a weight ratio from about 1.5:1 to about 3:1.

5. The solid pharmaceutical preparation according to claim 1, wherein the binder comprises a combination of vinylpyrrolidone-vinyl acetate copolymer and hydroxypropyl cellulose.

6. The solid pharmaceutical preparation according to claim 1, wherein dicalcium phosphate and the binder are present in relation to each other in a weight ratio from about 2:1 to about 1:0.01.

7. The solid pharmaceutical preparation according to claim 1, wherein dicalcium phosphate and the binder are present in relation to each other in a weight ratio from about 1:0.5 to about 1:0.07.

8. The solid pharmaceutical preparation according to claim 1, wherein the pharmaceutical preparation is in a granule, capsule, pellet, suppository, or tablet form.

9. The solid pharmaceutical preparation according to claim 8, wherein the pharmaceutical preparation is a tablet and further optionally comprises one or more pharmaceutically acceptable excipient selected from the group consisting of a filler, a disintegrant, a glidant, a lubricant, and a combination thereof.

10. The solid pharmaceutical preparation according to claim 9, wherein the tablet comprises 25 to 80% (w/w) of the pharmaceutically acceptable excipient; wherein the pharmaceutically acceptable excipient comprises about 0 to about 55% (w/w) of a filler, about 0 to about 20% (w/w) of a disintegrant, about 0 to about 7.5% (w/w) of a glidant, about 0 to about 5% (w/w) of a lubricant, based upon the total weight of the tablet, and wherein the pharmaceutically acceptable excipient optionally further comprises a total of about 0 to about 20% (w/w) of one or more additional pharmaceutically acceptable excipients, based upon the total weight of the tablet.

11. The solid pharmaceutical preparation according to claim 1, further comprising one or more water-soluble vitamins.

12. The solid pharmaceutical preparation according to claim 11, wherein the one or more water-soluble vitamins are vitamin B1, vitamin B6, vitamin B12 or a combination thereof.

13. The solid pharmaceutical preparation according to claim 12, wherein lipoic acid and the total of the one or more water-soluble vitamins are present in relation to each other in a weight ratio from about 1:0.1 to about 1:0.5.

14. A method for preparing the solid pharmaceutical preparation according to claim 1 using wet-granulation, wherein the method comprises:
 $a_1$) dissolving the binder in a solvent;
 $b_1$) spraying the solution obtained by step ($a_1$) onto the lipoic acid and dicalcium phosphate in a fluidized bed granulation and drying to form granules;
 c) collecting the granules obtained by step ($b_1$).

15. A method for preparing the solid pharmaceutical preparation according to claim 1 using wet-granulation, wherein the method comprises:
 $a_2$) mixing the binder, dicalcium phosphate and lipoic acid;
 $b_2$) spraying a solvent onto the mixture obtained in step $a_2$ in a fluidized bed granulation and drying to form granules; and
 c) collecting the granules obtained by step ($b_2$).

* * * * *